United States Patent [19]

Shoffner

[11] 4,157,343

[45] Jun. 5, 1979

[54] PREPARATION OF AROMATIC DIAMINES

[75] Inventor: James P. Shoffner, Elk Grove Village, Ill.

[73] Assignee: UOP Inc., Des Plaines, Ill.

[21] Appl. No.: 918,207

[22] Filed: Jun. 22, 1978

Related U.S. Application Data

[63] Continuation-in-part of Ser. No. 804,135, Jun. 6, 1977, abandoned.

[51] Int. Cl.$^2$ ............................................. C07C 85/18
[52] U.S. Cl. ............................... 260/570.9; 260/566 R
[58] Field of Search ............. 260/570.9, 570 R, 566 R

[56] References Cited

U.S. PATENT DOCUMENTS 2,750,416   6/1956   Exner et al. ..................... 260/570.9

*Primary Examiner*—Robert V. Hines
*Attorney, Agent, or Firm*—James R. Hoatson, Jr.; Raymond H. Nelson; William H. Page, II

[57] ABSTRACT

Aromatic diamines are prepared by reacting an alkyl formimine which has been obtained by the reaction of an amine possessing a primary or secondary alpha carbon atom with formaldehyde with an aromatic amine in an anhydrous acidic medium. The reaction is usually effected at ambient temperatures and atmospheric pressures and is exemplified by reacting n-hexylformimine with N,N-dimethylaniline in an anhydrous trifluoroacetic acid medium to form p-dimethylamino-N-n-hexylbenzylamine.

12 Claims, No Drawings

PREPARATION OF AROMATIC DIAMINES

CROSS-REFERENCE TO RELATED APPLICATIONS

This application is a continuation-in-part of my copending and now abandoned application Ser. No. 804,135 filed June 6, 1977, all teachings of which are incorporated herein by reference thereto.

BACKGROUND OF THE INVENTION

The prior art relating to the preparation of aromatic amines may be exemplified by U.S. Pat. No. 2,750,416. However, this patent teaches an azomethine-phenol mechanism utilizing formimines which have been derived from amines possessing a tertiary alpha-carbon atom, that is, the azomethine reactant possesses an alkyl substituent wherein the carbon atom which is directly attached to the nitrogen atom is completely substituted by other alkyl groups. The two components of the reaction mixture are admixed in reacting proportions or, if so desired, an inert organic solvent such as naphtha, benzene, or toluene may be present, although the presence of this solvent is said to be not required. The reason for utilizing this type of reactant, that is, a compound containing a tertiary alpha-carbon atom is that, in the past, it has been generally accepted that only those formimines in which the amino group is attached to a tertiary carbon atom will be sufficiently stable for isolation and for further reaction.

In contradistinction to the teachings set forth in the above-cited reference, it has now been discovered that formimines which have been prepared from alkyl amines where the alpha-carbon atom (the carbon atom directly bonded to the nitrogen atom) is primary or secondary may be utilized in a reaction with an aromatic amine to form the desired products of the present invention, that is, aromatic diamines. Formimines derived from such amines will hereinafter be referred to as primary and secondary alkyl formimines. In the case of primary alkyl formimines, the alpha-carbon atom directly bonded to the nitrogen atom possesses two hydrogen atoms while in the case of the secondary alkyl formimines the alpha-carbon atom possesses only one hydrogen atom.

This invention relates to the formation of aromatic diamines, and more specifically to the formation of the aforementioned diamines by reacting a primary or secondary alkyl formimine with a tertiary aromatic amine in an anhydrous medium.

The compounds of the present invention which comprise aromatic diamines will find a wide variety of uses as antioxidants or antiozonants for various organic substrates such as petroleum products such as heating oil, lubricating oil, gasoline, etc., or other products which are subjected to the action of oxygen or ozone such as natural rubber, synthetic rubber such as Buna S, etc. In addition, these compounds may also find use in the chemical industry as herbicides, fungicides, insecticides, etc.

It is therefore an object of this invention to provide a process for obtaining aromatic diamines, and particularly alkyl-substituted aromatic diamines.

A further object of this invention is to provide a process for obtaining aromatic diamines in which the reactants form the desired product in an anhydrous acidic medium.

In one aspect an embodiment of this invention resides in a process for the preparation of an aromatic diamine which comprises reacting a primary or secondary formimine, which is prepared by reacting a linear or branched chain primary alkyl amine with a formaldehyde to form said formimine reactant characterized by possession of a linear or branched chain alkyl moiety attached to the nitrogen atom of said formimine reactant, with a tertiary aromatic amine in an anhydrous acidic medium, and recovering the resultant aromatic diamine.

A specific embodiment of this invention is found in a process for the preparation of an aromatic diamine which comprises reacting formaldehyde with n-hexylamine at a temperature in the range of from about 20° to about 100° C. and a pressure in the range of from about atmospheric to about 100 atmospheres, reacting the resultant n-hexylformimine with N,N-dimethylaniline at a temperature in the range of from about 20° to about 100° C. and a pressure in the range of from about atmospheric to about 100 atmospheres in the presence of anhydrous trifluoroacetic acid, and recovering the resultant p-dimethylamino-N-n-hexylbenzylamine.

Other objects and embodiments will be found in the following further detailed description of the present invention.

As hereinbefore set forth the present invention is concerned with the process for preparing aromatic diamines by reacting an alkyl formimine with an aromatic tertiary amine, the reaction being effected in an anhydrous acidic medium. The formimine which is utilized as one of the starting materials of the present invention may be prepared by reacting a linear or branched chain primary alkyl amine containing from 1 to 10 carbon atoms with formaldehyde at reaction conditions which include a temperature ranging from 20° to about 100° C. and a pressure ranging from about atmospheric to about 100 atmospheres. In the preferred embodiment of the invention, the reaction conditions which are utilized will include ambient (about 20°–25° C.) temperature and atmospheric pressure. Examples of alkyl amines which may be reacted with formaldehyde, which may be in the form of paraformaldehyde, will include methylamine, ethylamine, n-propylamine, isopropylamine, isobutylamine, sec-butylamine, n-pentylamine, isopentylamine, 2-pentylamine, n-hexylamine, 2-hexylamine, 3-hexylamine, the corresponding primary and secondary heptyl-, octyl-, nonyl- and decylamines, etc. The formation of the formimine by reacting substantially equimolar amounts of the primary alkyl amine and the formaldehyde may be effected in the presence of an organic solvent, preferably one which is immiscible with water which is formed as a byproduct of the reaction. An example of this type of organic solvent which may be employed comprises methylene chloride.

In the past, formimines have not usually been considered for use in a Mannich reaction due to the tendency of the formimines to undergo self-condensation. This tendency is especially true when the carbon atom which is attached to the amino group is not completely substituted. However, it has now been discovered that it is not necessary to isolate or separate and purify further the alkyl formimine which is formed by the reaction between the primary alkyl amine and the formaldehyde prior to use as the reactant when treating a tertiary aromatic amine. The desired alkyl formimine may be used directly as a reactant, the only steps which are required for its use being a separation from the water of the formation and the removal of the relatively volatile and water immiscible solvent. By utilizing the formimine in this condition, it is possible to react the same with the tertiary aromatic amine at mild operating conditions of ambient temperature and pressure thus further inhibiting any formation of undesired or unwanted by-products. Another advantage which is attendant to the use of the present process is that relatively inexpensive reaction equipment may also be employed, if so desired, thus eliminating the need for high pressure or high temperature resistant equipment.

The primary and secondary alkyl formimines such as methylformimine, ethylformimine, n-propylformimine, n-butylformimine, isobutylformimine, sec-butylformimine, n-pentylformimine, isopentylformimine, n-hexylformimine, etc., which have been formed are then reacted with a tertiary aromatic amine, the reaction also being effected at temperatures ranging from about 20° to about 100° C. and pressures ranging from about atmospheric to about 100 atmospheres. Examples of tertiary aromatic amines which may be employed in the process of the present invention will include N,N-dimethylaniline, N,N-diethylaniline, N,N-di-n-propylaniline, N,N-diisopropylaniline, N,N-di-n-butylaniline, N,N-di-t-butylaniline, N,N-dipentylaniline, the isomeric dihexyl-, diheptyl-, dioctyl-, dinonyl-, and didecylanilines, etc.

The reaction of the alkyl formimine with the tertiary aromatic amine may be illustrated by the following series of equations.

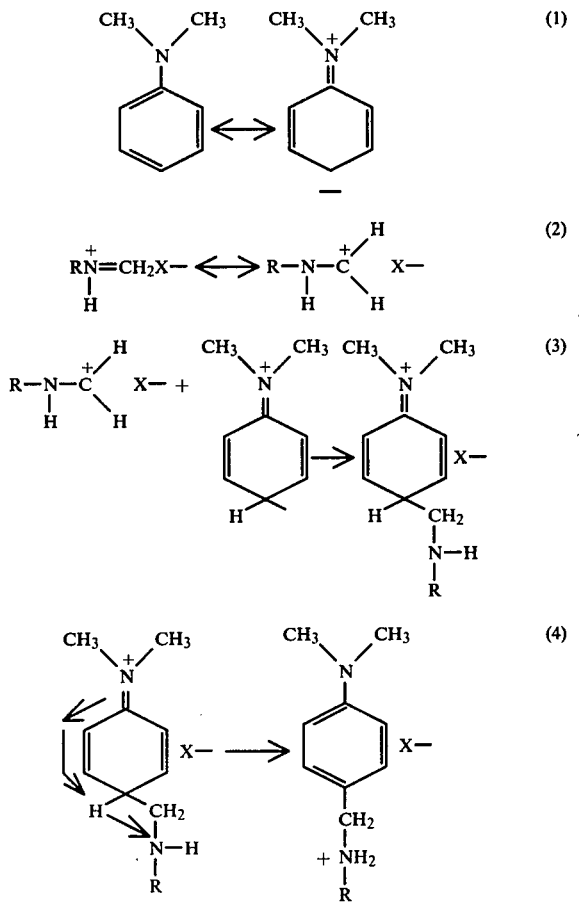

It is to be noted that there is no requirement for an acid cleavage of the formimine into formaldehyde and amine in order to achieve reaction inasmuch as in order to effect a cleavage of the formimine it is necessary that a mole of water be present for every mole of formimine which decomposes. As will hereinafter be set forth in greater detail, the reaction is effected in an anhydrous acidic medium, no water being present in the reaction medium.

Examples of acids which may be employed to provide the acidic medium in which the linear alkyl formimine and the tertiary aromatic amine are reacted will include organic acids such as formic acid, acetic acid, propionic acid, butyric acid, valeric acid, etc.; halogen substituted organic acids such as trichloroacetic acid, trifluoroacetic acid, trichloropropionic acid, trifluoropropionic acid, etc.; benzenesulfonic acid, p-toluenesulfonic acid, etc. In addition, it is also contemplated within the scope of this invention that inorganic acids which are anhydrous in nature may also be employed, such acids including anhydrous hydrogen chloride, anhydrous hydrogen bromide, anhydrous hydrogen iodide, ect. Futhermore, if so desired, the tertiary aromatic amine may be reacted with the alkyl formimine in the form of a mineral acid salt such as the chloride, bromide, sulfate, nitrate, phosphate, etc., salt, the only criterion being that the salt is in an anhydrous state when utilized as one of the reactants. The anhydrous acidic medium in which the reaction is effected is necessary in order that the employment of such a medium provides a mechanism wherein cleavage of the alkyl formimine is eliminated.

The preparation of the aromatic diamines may be effected in any suitable manner. When utilizing a batch type operation, a quantity of the primary alkyl amine of the type hereinbefore set forth in greater detail and formaldehyde, preferably in the form of paraformaldehyde, in equimolar amounts are placed in a suitable apparatus along with a solvent such as methylene chloride. In the preferred embodiment of this invention, the solvent which is employed will possess a low boiling point and a high degree of immiscibility with water which is formed during the reaction. The amine and formaldehyde are stirred while maintaining the temperature at the reflux temperature of the solvent. The reaction is allowed to proceed for a predetermined period of time which may range from about 0.5 up to about 10 hours or more in duration. At the end of this time, the mixture is allowed to stand without stirring and the water phase is separated from the organic phase. The organic phase is then dried over a drying agent such as calcium carbonate, sodium sulfate, etc., and the solvent is removed by suitable means such as evaporation, distillation, etc. Thereafter the alkyl formimine and the tertiary aromatic amine along with the acid such as an organic acid of the type hereinbefore set forth are placed in a second apparatus along with a solvent if so desired. The solvents which may be employed in this second step of the operation may include alcohols such as methyl alcohol, ethyl alcohol, n-propyl alcohol, isopropyl alcohol, etc., paraffins such as pentane, hexane, cyclopentane, cyclohexane, etc., and allowed to react at temperatures within the range previously set forth. It is also contemplated within the scope of this invention that superatmospheric pressures may be employed in the event that it is desired to utilize temperatures in the upper range of the scale. When utilizing superatmospheric pressures, said pressures are afforded by the introduction of an inert gas such as nitrogen, the reaction being effected in a pressure resistant vessel such as an autoclave. After allowing the reaction to proceed for a period ranging from 0.5 up to about 20 hours or more, the desired aromatic diamine is recovered and separated from any unreacted starting materials and acid by conventional means such as distillation, crystallization, etc. The salt is then neutralized and the desired aromatic diamine recovered therefrom.

Examples of aromatic diamines which may be prepared according to the process of this invention will include p-dimethylamino-N-methylbenzylamine, p-dimethylamino-N-ethylbenzylamine, p-dimethylamino-N-propylbenzylamine, p-dimethylamino-N-isopropylbenzylamine, p-dimethylamino-N-n-butylbenzylamine, p-dimethylamino-N-isobutylbenzylamine, p-dimethylamine-N-n-pentylbenzylamine, p-dimethylamino-N-n-hexylbenzylamine, p-dimethylamino-N-n-heptylbenzylamine, p-dimethylamino-N-n-octylbenzylamine, p-diethylamino-N-methylbenzylamine, p-diethylamino-N-ethylbenzylamine, p-diethylamino-N-propylbenzylamine, p-diethylamino-N-n-butylbenzylamine, p-diethylamino-N-n-pentylbenzylamine, p-diethylamino-N-isopentylbenzylamine, p-diethylamino-N-n-hexylbenzylamine, p-diethylamino-N-n-heptylbenzylamine, p-dipropylamino-N-methylbenzylamine, p-dipropylamino-N-ethylbenzylamine, p-dipropylamino-N-n-propylbenzylamine, p-dipropylamino-N-n-butylbenzylamine, p-dipropylamino-N-isobutylbenzylamine, p-dipropylamino-N-n-pentylbenzylamine, p-dipropylamino-N-n-hexylbenzylamine, p-dipropylamino-N-n-heptylbenzylamine, p-dipropylamino-N-n-octylbenzylamine, p-di-t-butylamino-N-methylbenzylamine, p-di-t-butylamino-N-n-ethylbenzylamine, p-di-t-butylamino-N-n-propylbenzylamine, p-di-t-butylamino-N-n-butylbenzylamine, p-di-n-pentylamino-N-t-butylbenzylamine, p-di-t-butylamino-N-n-hexylbenzylamine, p-di-t-butylamino-N-n-heptylbenzylamine, p-dihexylamino-N-methylbenzylamine, p-dihexylamino-N-ethylbenzylamine, p-dihexylamino-N-propylbenzylamine, p-dihexylamino-N-n-butylbenzylamine, p-dihexylamino-N-n-pentylbenzylamine, p-dihexylamino-N-n-pentylbenzylamine, p-dihexylamino-N-n-hexylbenzylamine, etc. It is to be understood that these aromatic diamines are only representative of the class of compounds which may be prepared and that the present invention is not necessarily limited thereto.

The following examples are given for purposes of illustrating the process of the present invention. However, it is to be understood that these examples are only for purposes of illustration and that the present invention is not necessarily limited thereto.

EXAMPLE I

In this example 0.5 mole of n-hexylamine and 0.5 mole of formaldehyde in 150 ml of methylene chloride were stirred at reflux temperature (about 40° C.) until all of the solid was dissolved. Following this, the mixture was then transferred to a separatory funnel and after allowing it to stand the water was separated from the organic phase. The organic phase which contained the n-hexylformimine was dried over sodium sulfate. After removal of the methylene chloride solvent by evaporation at water bath temperature, the n-hexylformimine was then used to prepare the desired product.

The desired aromatic diamine was prepared by placing equimolar quantities of N,N-dimethylaniline and n-hexylformimine in 150 ml of methyl alcohol which contained an equimolar quantity of trifluoroacetic acid. The mixture was allowed to stand for a period of 16 hours at room temperature following which the solution was concentrated by evaporation of the methyl alcohol to give the trifluoroacetic acid salt of p-dimethylamino-N-n-hexylbenzylamine.

The blue salt was subjected to nuclear magnetic resonance spectrum analysis, said spectrum showing resonances at 1.02$\delta$ (CH$_3$, 3 protons); 1.45$\delta$ (CH$_2$, 6 protons); 1.89$\delta$ (CH$_2$, 2 protons); 2.78$\delta$ (CH$_2$, 2 protons); 3.21$\delta$ (CH$_3$, 6 protons), 4.28$\delta$ (CH$_2$, 2 protons); 6.20 and 6.97$\delta$ (aryl, 4 protons). In addition, it was found that there were broad resonances for three exchangeable protons underneath the aromatic resonances. The salt was neutralized by the addition of 10% sodium hydroxide solution and extracted with benzene. Upon evaporation of the benzene, a residue which crystallized immediately was collected. The nuclear magnetic resonance spectrum was run in deuterchloroform and showed the same resonances which were found for the salt, only slightly shifted in the free base.

EXAMPLE II

In this example 0.5 mole of isobutylamine and 0.5 mole of formaldehyde in the form of paraformaldehyde in 150 ml of methylene chloride were stirred at room temperature until all of the paraformaldehyde had dissolved. The water which formed during the reaction was separated, measured and found to be about 9 ml or an equivalent amount to indicate complete reaction. The solution of methylene chloride was dried and the solvent removed by rotary evaporation at a bath temperature of 38° C. The product was subjected to a nuclear magnetic resonance analysis, the spectrum of the product showing that it was the desired isobutylformimine.

Following this, equimolar quantities of N,N-dimethylaniline and isobutylformimine were placed in 125 ml of methylalcohol containing a molar equivalent of trifluoroacetic acid. The mixture was allowed to stand for a period of 16 hours at room temperature, after which the solution was concentrated to give the trifluoroacetic acid salt of p-dimethylamino-N-isobutylbenzylamine. This salt was neutralized with 10% of sodium hydroxide and the free base was extracted with chloroform. The solution was dried, the chloroform was removed and a nuclear magnetic analysis was run on the free base.

The NMR analysis showed a doublet at 0.94$\delta$ (2-CH$_3$, 6 protons), a doublet at 2.39$\delta$ (CH$_2$, 2 protons), a singlet at 2.93$\delta$ (2-CH$_3$, 6 protons), a singlet at 3.69$\delta$ (CH$_2$, 2 protons), A$_2$B$_2$ pattern at 6.76 and 7.29$\delta$ (aromatic, 4 protons), which indicated the presence of the desired compound p-dimethylamino-N-isobutylbenzylamine.

EXAMPLE III

A formimine may be prepared by reacting equimolar proportions of n-octylamine and paraformaldehyde dissolved in methylene chloride at reflux conditions until all of the solid dissolves. Upon completion of the reaction, the mixture may be allowed to stand until the water layer has separated from the organic layer. Thereafter the water layer may be removed and the methylene chloride layer dried over calcium carbonate. Following this, the methylene chloride may be removed by evaporation and the n-octylformimine which is formed is reacted with an equimolar quantity of N,N- di-t-butylaniline. The reaction may be effected in a methyl alcohol solution using trichloroacetic acid to provide the acidic medium. After thoroughly admixing the components of the reaction mixture, it may be allowed to stand for a period of 16 hours at room temperature. At the end of this time, the solvent may be removed by evaporation or distillation and the trichloroacetic acid salt of p-di-t-butylamino-N-n-octylbenzylamine may be recovered. If so desired, a free base may be prepared by neutralizing the aforesaid salt with a base. Other condensations which utilize formic acid or anhydrous hydrogen chloride gas to provide the acidic medium may give similar results.

EXAMPLE IV

In this example a formimine may be prepared by reacting equimolar quantities of n-butylamine and paraformaldehyde utilizing methylene chloride as the reaction medium, the reaction being effected at reflux temperatures for a period of time which is sufficient to dissolve the solid. At the end of the reaction period the mixture may be transferred to a separatory funnel and the water of formation may then be separated from the organic phase. The organic phase may then be dried over sodium sulfate and the methylene chloride removed by evaporation. Following this equimolar quantities of the thus formed n-butylformimine and N,N-diethylaniline may then be reacted in a methyl alcohol solution which contains trifluoroacetic acid. After admixing the reactants in a thorough manner at room temperature, the reactants may then be allowed to stand for a period of 16 hours. At the end of this period the trifluoroacetic acid salt may be recovered after separation and removal of the methyl alcohol, if so desired, may be neutralized with a base and the desired product comprising p-diethylamino-N-n-butylbenzylaniline may be recovered.

EXAMPLE V

In a manner similar to that set forth in the above example, the desired formimine may be prepared by reacting equimolar quantities of n-propylamine and paraformaldehyde using methylene chloride as the reaction medium in which the solids are dissolved. The reaction may be effected at reflux temperature for a period of time sufficient to dissolve the solids, at the end of which time the mixture may be transferred to a separatory funnel and the water of formation separated from the organic phase. The organic phase may then be dried over sodium sulfate and the methylene chloride removed by evaporation. The thus formed n-propyl formimine may be reacted with N,N-dimethylaniline in equimolar quantities in methyl alcohol which contains trifluoroacetic acid to provide the acidic portion of the reaction medium. After thorough admixing and allowing to stand for a period of 16 hours, the trifluoroacetic acid salt may be recovered after separation and removal of the methyl alcohol. The acid salt may then be neutralized with a base and the desired product comprising p-dimethylamino-N-n-propylbenzylaniline recovered therefrom.

EXAMPLE VI

In a like manner, equal molar quantities of 2-pentylamine and paraformaldehyde may be reacted using methylene chloride as the reaction medium in which the solids are dissolved at room temperature until all of the paraformaldehyde is dissolved, the water which forms during the reaction may be separated and the methylene chloride solution dried. The solvent may be removed by evaporation at an elevated temperature following which the 2-pentylformimine may be reacted with N,N-diethylaniline in equimolar quantities in a medium comprising methyl alcohol which contains trifluoroacetic acid. After thorough admixing and allowing to stand for a period of 16 hours, the trifluoroacetic acid salt may be recovered, neutralized with a base and the desired product comprising p-diethylamino-N-2-pentylbenzylaniline recovered therefrom.

I claim as my invention:

1. A process for the preparation of an aromatic diamine which comprises reacting a primary or secondary formimine, which is prepared by reacting a linear or branched chain primary alkyl amine with a formaldehyde to form said formimine reactant characterized by possession of a linear or branched chain alkyl moiety attached to the nitrogen atom of said formimine reactant, with a tertiary aromatic amine in an anhydrous acidic medium, and recovering the resultant aromatic diamine.

2. The process as set forth in claim 1 in which the reaction between said alkyl formimine and said tertiary aromatic amine is effected at a temperature in the range of from about 20° to about 100° C. and a pressure in the range of from about atmospheric to about 100 atmospheres.

3. The process as set forth in claim 1 in which said anhydrous acidic medium is afforded by the presence of trichloroacetic acid.

4. The process as set forth in claim 1 in which said anhydrous acidic medium is afforded by the presence of trifluoroacetic acid.

5. The process as set forth in claim 1 in which said anhydrous acidic medium is afforded by the presence of formic acid.

6. The process as set forth in claim 1 in which said anhydrous acidic medium is afforded by the presence of hydrogen chloride gas.

7. The process as set forth in claim 1 in which said alkyl formimine is a reaction product of formaldehyde with a linear primary amine selected from the group consisting of methylamine, ethylamine, n-propylamine, n-butylamine, n-pentylamine and n-hexylamine.

8. The process as set forth in claim 1 in which said alkyl formimine is n-hexylformimine and said aromatic amine is N,N-dimethylaniline.

9. The process as set forth in claim 1 in which said alkyl formimine is n-butylformimine and said aromatic amine is N,N-diethylaniline.

10. The process as set forth in claim 1 in which said alkyl formimine is n-propylformimine and said aromatic amine is N,N-dimethylaniline.

11. The process as set forth in claim 1 in which said alkyl formimine is isobutylformimine and said aromatic amine is N,N-dimethylaniline.

12. The process as set forth in claim 1 in which said alkyl formimine is 2-pentylformimine and said aromatic amine is N,N-diethylaniline.

* * * * *